United States Patent
Weinberg et al.

(10) Patent No.: US 7,212,857 B2
(45) Date of Patent: May 1, 2007

(54) IMPLANTABLE CARDIAC DEVICE FOR RESTORING INTER-CHAMBER SYNCHRONY AND METHOD

(75) Inventors: Lisa P. Weinberg, Moorpark, CA (US); Richard Lu, Thousand Oaks, CA (US)

(73) Assignee: Pacesetter, Inc., Sylmar, CA (US)

( * ) Notice: Subject to any disclaimer, the term of this patent is extended or adjusted under 35 U.S.C. 154(b) by 624 days.

(21) Appl. No.: 10/136,916

(22) Filed: May 1, 2002

(65) Prior Publication Data

US 2003/0208238 A1    Nov. 6, 2003

(51) Int. Cl.
*A61N 1/368*    (2006.01)
(52) U.S. Cl. .......................................... 607/9; 607/15
(58) Field of Classification Search .................... 607/9, 607/15, 14; 600/509
See application file for complete search history.

(56) References Cited

U.S. PATENT DOCUMENTS

| | | | |
|---|---|---|---|
| 4,928,688 A * | 5/1990 | Mower | 607/9 |
| 5,466,254 A | 11/1995 | Helland | 607/123 |
| 5,720,768 A * | 2/1998 | Verboven-Nelissen | 607/9 |
| 5,800,465 A | 9/1998 | Thompson et al. | 607/9 |
| 5,902,324 A | 5/1999 | Thompson et al. | 607/9 |
| 5,978,705 A | 11/1999 | KenKnight et al. | 607/5 |
| 6,021,351 A | 2/2000 | Kadhiresan et al. | 607/19 |
| 6,081,748 A | 6/2000 | Struble et al. | 607/9 |
| 6,122,545 A | 9/2000 | Struble et al. | 607/9 |
| 6,622,040 B2 * | 9/2003 | Ding et al. | 607/9 |

FOREIGN PATENT DOCUMENTS

WO    WO 99/55414    11/1999
WO    WO 99/55415    11/1999

* cited by examiner

*Primary Examiner*—Kennedy Schaetzle

(57) ABSTRACT

An implantable cardiac device returns activations of corresponding right and left chambers of a heart to inter-chamber synchrony. A sensing circuit senses intracardiac signals representing right and left chamber ventricular electrical activity. A detector determines if a predetermined characteristic of the electrogram signals indicates dissociation of the corresponding right and left chambers. If dissociation is indicated, a pulse generator stimulates at least one of the corresponding chambers to restore inter-chamber synchrony.

105 Claims, 7 Drawing Sheets

IMPLANTABLE CARDIAC DEVICE FOR RESTORING INTER-CHAMBER SYNCHRONY AND METHOD

FIELD OF THE INVENTION

This application is related to copending U.S. patent application Ser. No. 10/137,604, filed May 1, 2002, titled "Implantable Cardiac Stimulation Device Which Recommends Ablation Therapy and Method".

FIELD OF THE INVENTION

The invention generally relates to implantable cardiac stimulation devices, and in particular, to techniques for restoring inter-chamber synchrony to prevent tachyarrhythmias.

BACKGROUND OF THE INVENTION

A dysrhythmia is an abnormal heart beat pattern. One example of a dysrhythmia is a bradycardia wherein the heart beats at an abnormally slow rate or wherein significant pauses occur between consecutive beats. Other examples of dysrhythmias include tachyarrhythmias wherein the heart beats at an abnormally fast rate. With atrial tachycardia, the atria of the heart beat abnormally fast. With ventricular tachycardia (VT) the ventricles of the heart beat abnormally fast. Though often unpleasant for the patient, a tachycardia is typically not fatal. However, some tachycardias, particularly ventricular tachycardia, can trigger ventricular fibrillation wherein the heart beats chaotically such that there is little or no net flow of blood from the heart to the brain and other organs. Ventricular tachycardia, if not terminated, is fatal. Hence, it is highly desirable to prevent or terminate dysrhythmias, particularly ventricular tachycardias.

One technique for preventing or terminating dysrhythmias is to overdrive pace the heart wherein an implantable cardiac stimulation device, such as a pacemaker or implantable cardioverter defibrillator (ICD), applies electrical pacing pulses to the heart at a rate somewhat faster than the intrinsic heart rate of the patient. For bradycardia, the cardiac stimulation device may be programmed to artificially pace the heart at a rate of 60 to 80 pulses per minute (ppm) to thereby prevent the heart from beating too slow and to eliminate any long pauses between heart beats. To prevent tachyarrhythmias from occurring, the cardiac stimulation device artificially paces the heart at a rate of at least five to ten pulses per minute faster than the intrinsic tachyarrhythmia heart rate of the patient. In other words, a slight artificial tachycardia is induced and maintained in an effort to prevent an actual tachycardia from arising. If an actual tachycardia occurs, such as a supraventricular tachycardia (SVT) wherein the heart beats at 150 beats per minute or more, the cardiac stimulation device senses tachycardia and immediately begins pacing at a rate of at least five to ten pulses per minute (ppm) faster than the tachycardia and then slowly decreases the pacing rate in an effort to slowly reduce the heart rate back to a normal resting rate, thereby terminating the tachycardia.

Many patients who suffer from tachyarrhythmias have had episodes of ischemia wherein blood flow to the ventricular myocardium is reduced or blocked due to narrowing or occlusion of a coronary artery. This causes myocardial scarring, believed to present re-entrant circuits that can be triggered into sustained ventricular tachycardia or ventricular fibrillation by introduction of premature ventricular contractions (PVCs). A PVC is a ventricular contraction which is not preceded by a coupling atrial contraction (P wave). It is also at times assumed that a clinical episode of monomorphic ventricular tachycardia is also initiated by spontaneous PVCs. This assumption is reinforced by the known relationship between PVCs and sudden cardiac death. It would thus be beneficial if implantable cardiac devices could prevent PVCs from triggering ventricular tachyarrhythmias.

It is believed that dissociation between the left ventricle and the right ventricle may be responsible for PVCs. Further, it is believed that changes in the QRS complex on a surface electrocardiogram is the result of a dissociation in inter-chamber delay as, for example, the inter-ventricular delay ($V_R$-$V_L$ Delay) or inter-atrial delay ($A_R$-$A_L$ Delay). For example, the widening of the QRS complex (as is sometimes seen in monomorphic VT) may be the result of an increase in the $V_R$-$V_L$ Delay. Furthermore, alternating amplitude of the QRS complex (as is sometimes seen in polymorphic VT) or P waves may be the result of a more significant dissociation in the $V_R$-$V_L$ Delay or $A_R$-$A_L$ Delay, respectively. It is further believed that if the $V_R$-$V_L$ Delay becomes too great, then total dissociation between the left and right ventricles of the heart will result in a ventricular fibrillation and perhaps sudden cardiac death and that if the $A_R$-$A_L$ Delay becomes too great, then total dissociation between the left and right atria of the heart will result in atrial fibrillation. It is still further believed that significant variability of inter-chamber delay, either of the ventricles or the atria, may also be prone to the development of ventricular fibrillation.

SUMMARY OF THE INVENTION

The invention therefore provides an implantable cardiac device and method wherein potential dissociation of corresponding right and left chambers of a heart is detected and corrective therapy to restore inter-chamber synchrony is initiated.

More particularly, the present invention provides an implantable cardiac device that returns activations of corresponding right and left chambers of a heart to inter-chamber synchrony. The device includes a sensing circuit that generates electrogram signals representing electrical activity of the corresponding right and left chambers, a detector responsive to the electrogram signals that detects a predetermined characteristic of the electrogram signals indicative of dissociation of the corresponding right and left chambers, and a pulse generator that stimulates at least one of the corresponding right and left chambers to restore inter-chamber synchrony of the corresponding right and left chambers responsive to the detector detecting the predetermined characteristic. The corresponding right and left chambers may be the right and left ventricles or the right and left atria.

The predetermined characteristic may be a premature ventricular contraction wherein the detector includes a premature ventricular contraction detector, and wherein the pulse generator is configured to apply a stimulation pulse to one of the right ventricle and left ventricle responsive to the detector detecting a premature ventricular contraction in the other one of the right ventricle and left ventricle.

The predetermined characteristic may be a change in right chamber activation to left chamber activation time, and wherein the detector includes a timer that times the right chamber activation to left chamber activation time during successive cardiac cycles. The change in right chamber activation to left chamber activation time may be an increase in right chamber activation to left chamber activation time.

The increase may be a sudden increase or a gradual increase to a threshold value. The change may alternatively be instability in the right chamber activation to left chamber activation time over successive cardiac cycles.

The predetermined characteristic may be a change in order of right chamber and left chamber activation from a normal order, such as from right ventricular to left ventricular activation, and wherein the pulse generator applies pacing pulses to at least one of the right chamber and the corresponding left chamber to restore the order of activation to the normal order.

The predetermined characteristic may be a relative amplitude difference between a right chamber activation and a left chamber activation within a common cardiac cycle and wherein the pulse generator is a pacing pulse generator that overdrive paces at least one of the right chamber and left chamber in response to the detector detecting a relative amplitude difference greater than a predetermined factor.

The invention further provides a method of detecting inter-chamber dissociation of a heart and restoring inter-chamber synchrony to the heart. The method includes the steps of sensing electrical activity of corresponding right and left chambers of a heart and generating electrical signals representing electrical activity of the right and left chambers, detecting a predetermined characteristic in the electrical signals indicative of inter-ventricular dissociation, and applying stimulating pulses to at least one of the right and left chambers of the heart to restore inter-chamber synchrony responsive to detecting the predetermined characteristic.

BRIEF DESCRIPTION OF THE DRAWINGS

Further features and advantages of the present invention may be more readily understood by reference to the following description taken in conjunction with the accompanying drawings, in which.

DESCRIPTION OF THE PREFERRED EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
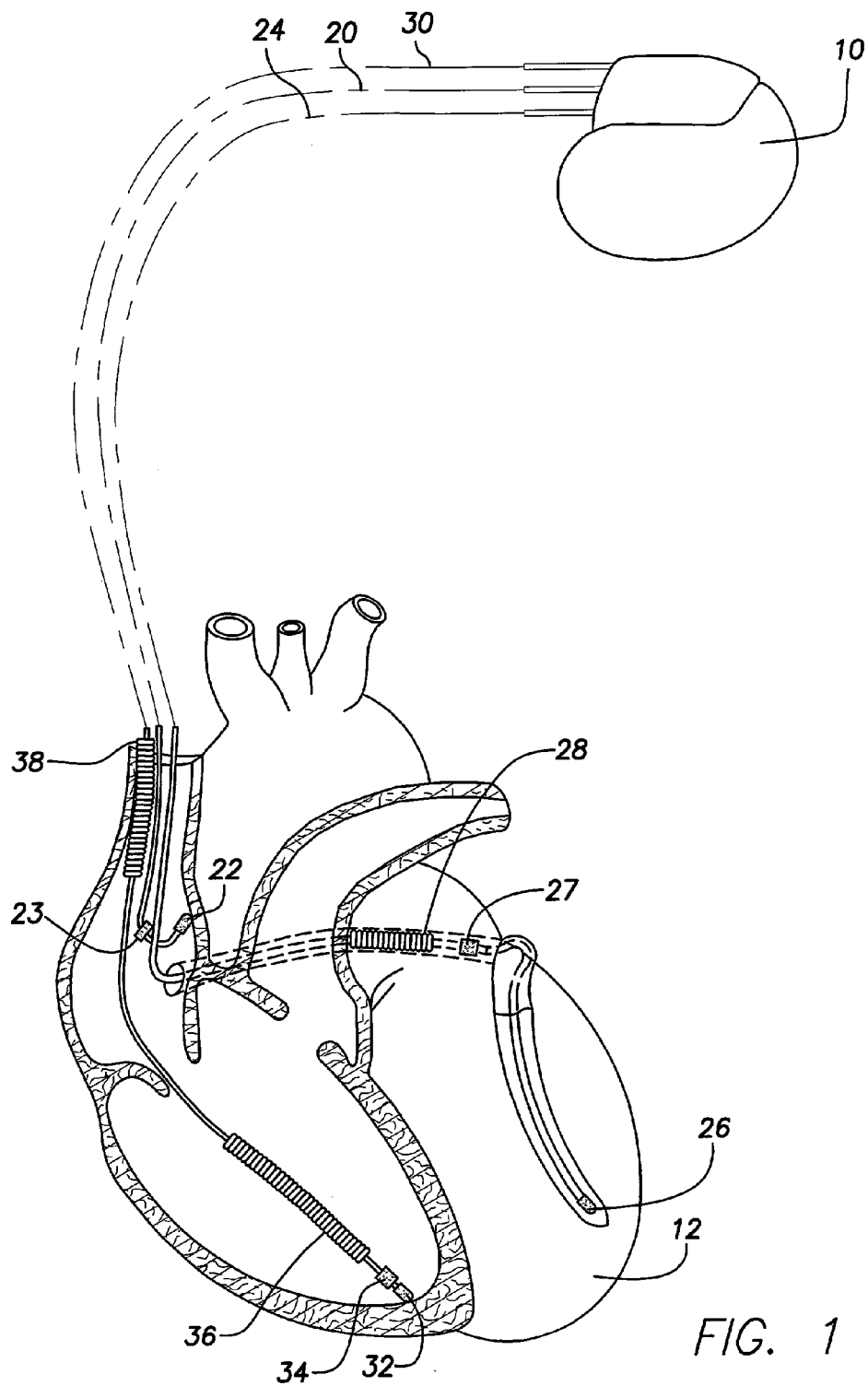
FIG. 1 is a simplified diagram illustrating an implantable stimulation device embodying the present invention in electrical communication with at least three leads implanted into a patient's heart for delivering multi-chamber stimulation and shock therapy.

As shown in FIG. 1, there is a stimulation device 10 embodying the present invention in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having a right atrial tip electrode 22, typically implanted in the patient's right atrial appendage, and a right atrial ring electrode 23.

To sense left atrial and ventricular cardiac signals and to provide left chamber pacing therapy, the stimulation device 10 is coupled to a "coronary sinus" lead 24 designed for placement in the "coronary sinus region" via the coronary sinus ostium for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28. For a complete description of a coronary sinus lead, see U.S. patent application Ser. No. 09/457,277, filed Dec. 8, 1999, entitled "A Self-Anchoring, Steerable Coronary Sinus Lead" (Pianca et al.); and U.S. Pat. No. 5,466,254, "Coronary Sinus Lead with Atrial Sensing Capability" (Helland), which patents are hereby incorporated herein by reference.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
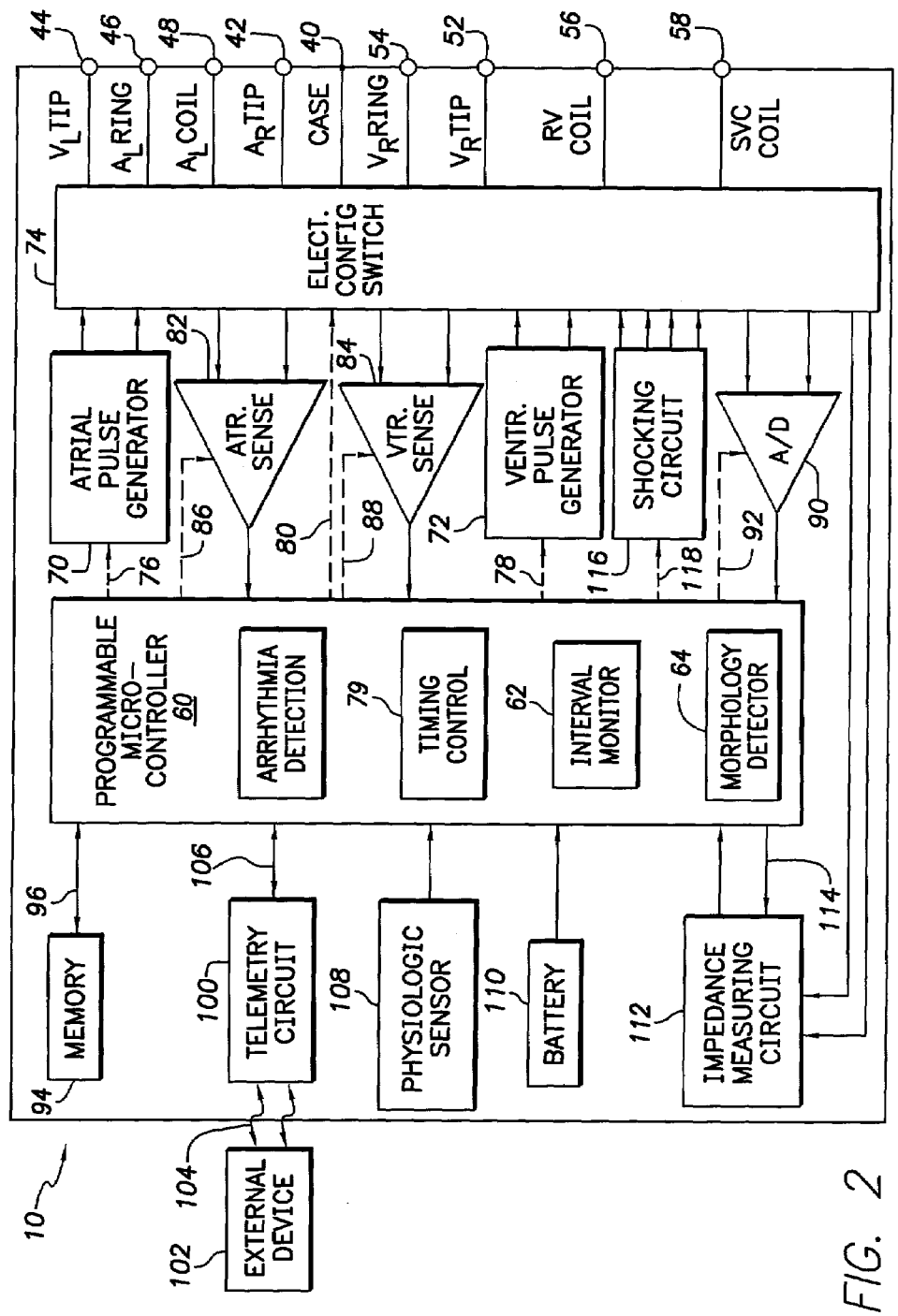
FIG. 2 is a functional block diagram of a multi-chamber implantable stimulation device embodying the present invention illustrating the basic elements of a stimulation device which can provide cardioversion, defibrillation and pacing stimulation in four chambers of the heart.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses.

The stimulation device additionally includes a battery 110 which provides operating power to all of the circuits shown in FIG. 2. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected.

As further shown in FIG. 2, the device 10 is shown as having an impedance measuring circuit 112 which is enabled by the microcontroller 60 via a control signal 114. The impedance measuring circuit 112 is not critical to the present invention and is shown for only completeness.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5–10 Joules), or high energy (11 to 40 Joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Now that the exemplary implantable cardiac device 10 has been generally described, the following description of the device is more particularly directed to those aspects of the device 10 which enable the device to implement the therapy contemplated by the present invention. As previously described, the present invention is broadly directed to the prevention of tachyarrhythmias by restoring inter-chamber synchrony. More particularly, the device 10 detects indicative dissociation of the right and left ventricles or right and left atria and in response to such detection, applies stimulation to one or both of the ventricles or atria to restore ventricular synchrony.

In a healthy heart, an activation of the right ventricular (a right ventricular R wave) is generally followed by a left ventricular activation (a left ventricular R wave) within a normal inter-ventricular delay interval of about, for example, 10 to 50 milliseconds. Dissociation of the right ventricle and the left ventricle may be indicated by an abrupt or gradual increase in the inter-ventricular delay, instability of the inter-ventricular delay or a change in the activation sequence of the ventricles from a normal activation sequence. Any one of these conditions can disrupt the ventricular refractoriness and promote dispersion of refractoriness rendering the ventricles vulnerable to tachyarrhythmias such as ventricular tachycardia or ventricular fibrillation. The above applies equally well to the atria. It is further also likely that PVCs may be caused by ventricular dissociation.

In view of the above, the present invention contemplates the sensing of intracardiac signals representing the electrical activity of corresponding right and left chambers of the heart, detecting a predetermined characteristic in the intracardiac signals indicative of inter-chamber dissociation, and the stimulating of one or both of the corresponding chambers to restore inter-ventricular synchrony. As will be seen hereinafter, the predetermined characteristic may be the occurrence of a PVC, a sudden increase in the inter-chamber delay, a gradual increase in the inter-chamber delay, an instability in the inter-chamber delay, a change in the inter-chamber activation sequence, or a relatively large difference in right chamber activation and corresponding left chamber activation amplitudes. For determining inter-chamber delays, even markers may be utilized in a manner well known in the art. The stimulation applied to the heart depends on the particular characteristic of dissociation detected.

Returning now to FIG. 2, and in accordance with the present invention, in the embodiment illustrated, the electrogram signals representing the electrical activity of the right and left ventricles or right and left atria are generated by the data acquisition system 90. Preferably, for both inter-ventricular and inter-atrial monitoring, the data acquisition systems generates at least two electrograms. For ventricular monitoring, the right ventricular electrodes 34 and 32 generate a right ventricular electrogram and the left ventricular electrode 26 and the case 40 generate a left ventricular electrogram. For atrial monitoring, the right atrial electrodes 22 and 23 generate a right atrial electrogram and the left atrial electrodes 27 and 28 generate a left atrial electrogram.

The electrogram signals thus generated are analyzed by the microprocessor 60. To that end, the microprocessor 60 includes an interval monitor stage 62. The stage 62 is preferably capable of determining the time or interval between the ventricular activations and atrial activation of each cardiac cycle and determining the difference between those intervals over a number of successive cardiac cycles. This enables the microprocessor 60 to determine a sudden increase in inter-chamber delay or a gradual increase in the inter-chamber delay to a threshold delay. Still further, this enables the microprocessor 60 to determine instability in the inter-chamber delay by using variability, for example, well known in the art. The microprocessor is also able to discern both a normal inter-chamber activation sequence and a change or reversal from that sequence.

The microprocessor 60 further includes a morphology detector 64. The detector 64, of a type well known in the art, may be employed for detecting PVCs. As is well known, the morphology of PVCs is quite different than that of normal sinus R waves. Hence, by comparing each ventricular activation to a normal sinus R wave template, the detector 64 is able to discern the occurrence of a PVC in one of the ventricles. PVCs may be detected with other techniques as are known in the art without departing from the present invention. For example, a PVC may be detected by noting a ventricular activation in either ventricle which is not immediately preceded by a coupling P wave or by detecting an R wave which falls within an "early window".

Additionally or alone, the microprocessor 60 may discern dissociation of corresponding chambers by noting when the amplitudes of the corresponding right and left chamber activations are radically different. Here, the electrograms are analyzed by the microprocessor during each cardiac cycle for a disparity in right and left chamber activation amplitude.

In accordance with this embodiment, the pulse generator 72 applies the stimulation pulses to one or both ventricles or atria to restore inter-chamber synchrony. The pulse generator 72 times delivery of the stimulation pulses under control of the timing control 79. That control may determine the delivery time of a single stimulation pulse or cause the pulse generator 72 to stimulate one or both of the ventricles or atria in an overdrive pacing mode.

Figure 3:
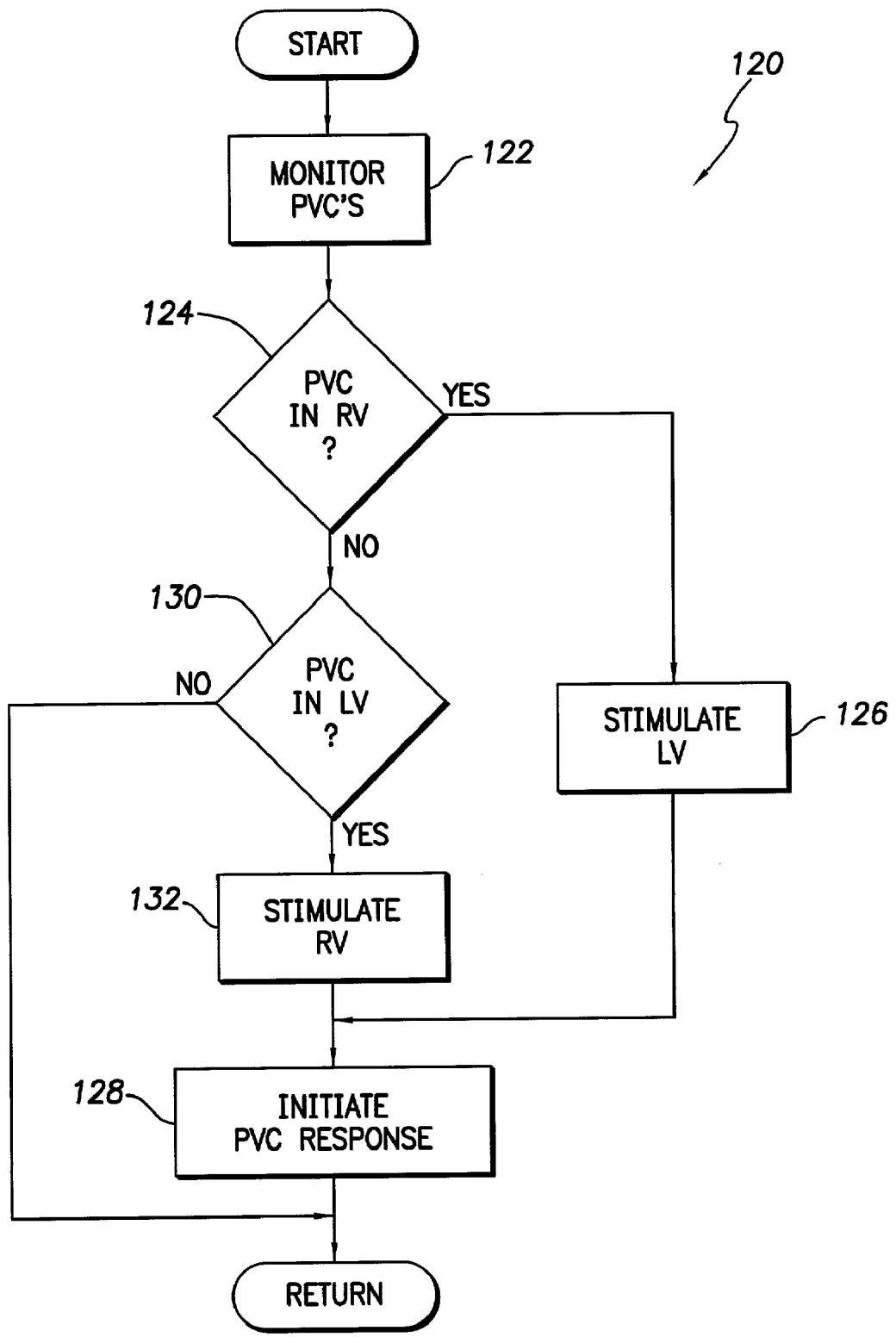
FIG. 3 is a flow chart describing an overview of the operation of one embodiment of the present invention wherein PVCs are detected and corrective stimulation pulses are applied to the heart.

In FIG. 3, a flow chart 120 is shown describing an overview of the operation and novel features implemented in one embodiment of the device 10. In this flow chart, and the other flow charts described herein, the various algorithmic steps are summarized in individual "blocks". Such blocks describe specific actions or decisions that must be made or carried out as the algorithm proceeds. Where a microcontroller (or equivalent) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein.

The process of FIG. 3 initiates with PVC monitoring in activity block 122. In implementing activity block 122 the morphology detector 64 detects for PVCs in both the right and left ventricle by conventional techniques, such as, the detection of an R-wave not preceded by a P-wave, or an R-wave that falls in a predefined early window, or by template matching utilizing the electrogram signals generated by the data acquisition system 90.

The process next determines, in decision block 124, if a PVC is detected in the right ventricle. If a PVC is detected in the right ventricle, the process immediately advances to activity block 126 for stimulating the left ventricle. Activity block 126 is carried out by the pulse generator 72 applying a pacing stimulation pulse, under timing control of timing control 79, to the left ventricle. The pacing pulse is applied to the left ventricle a delay time after the occurrence of the PVC in the right ventricle. The delay time preferably is within a normal inter-ventricular delay interval of, for example, 10 to 50 milliseconds, or is a predetermined normal delay time determined over time from a number of normal sinus inter-ventricular delay intervals of the patient. By stimulating the left ventricle a normal delay time after the occurrence of the PVC in the right ventricle, inter-ventricle synchrony is restored.

Following activity block 126, the process advances to activity block 128. Here, a PVC response is initiated to prevent a pacemaker mediated tachycardia. Such responses contemplated by activity block 128 are well known in the art.

If in decision block 124 it is determined that a PVC has not occurred in the right ventricle, the process advances to decision block 130. Here it is determined if a PVC has occurred in the left ventricle. If a PVC is not detected in the left ventricle, the process returns. However, if a PVC is detected in the left ventricle, the process immediately advances to activity block 132 for stimulating the right ventricle. Activity block 132 is carried out by the pulse generator 72 applying a pacing stimulation pulse, under timing control of timing control 79, to the right ventricle. The pacing pulse is applied to the right ventricle a delay time after the occurrence of the PVC in the left ventricle. The delay time preferably is within a normal inter-ventricular delay interval of, for example, 10 to 50 milliseconds, or is a predetermined normal delay time determined over time from a number of normal sinus inter-ventricular delay intervals of the patient. By stimulating the right ventricle a normal delay time after the occurrence of the PVC in the left ventricle, inter-ventricle synchrony is restored.

Following activity block 132, the process advances to activity block 128 to initiate the PVC response for preventing a pacemaker mediated tachycardia. The process then returns.

While FIG. 3 has been described with reference to the ventricle, it is within the spirit of the invention to modify FIG. 3 to reflect monitoring premature atrial contractions (PAC's), detecting which chamber the PAC occurred in, and then stimulating the opposite chamber according to a "PAC response" such as atrial overdrive pacing.

Figure 4:
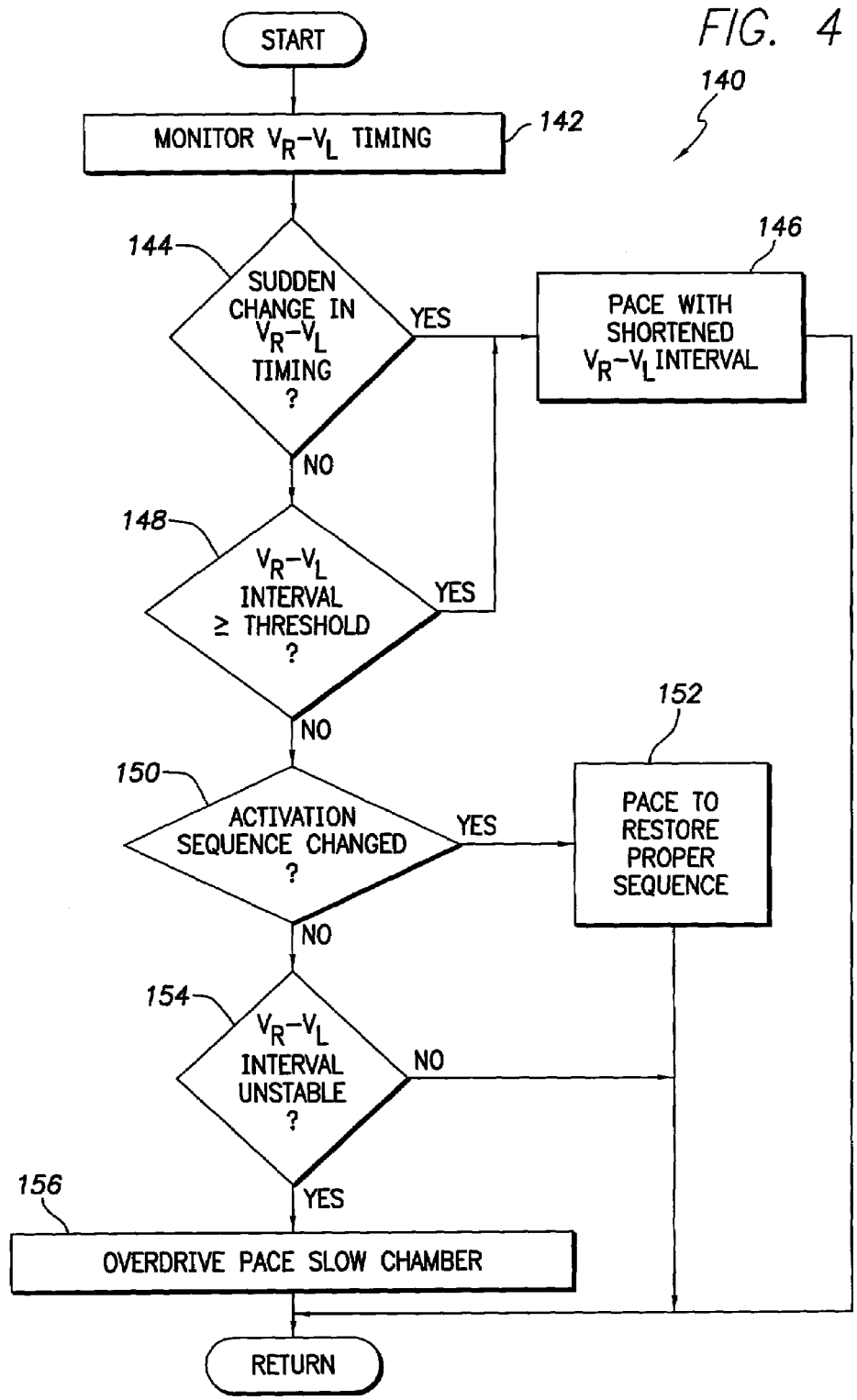
FIG. 4 is a flow chart describing an overview of the operation of another embodiment of the present invention wherein right ventricular and left ventricular activation timing is monitored and corrective stimulation is applied to the heart.

FIG. 4 shows a flow chart 140 describing an embodiment of the present invention based upon right ventricular and left ventricular activation timing. Hence the process initiates with the timing of the right ventricular and left ventricular activations in activity block 142. In decision block 144 it is determined if there has been a sudden change in the inter-ventricular delay interval. This determination may be made on a cycle to cycle basis or may be based on a change in the inter-ventricular delay over a limited number of cycles, for example, three cycles. The sudden change is preferably an increase of more than, for example 50 to 100 milliseconds. Alternatively the sudden increase may be based upon a percentage of a normal inter-ventricular delay of the patient.

If there is a sudden increase in the inter-ventricular interval determined in decision block 144, the process advances to activity block 146 for returning the ventricles to inter-ventricular synchrony. Here it is contemplated that the ventricles be overdriven with a shortened inter-ventricular delay. The delay may be less than normal for the patient and may be incrementally increased to a normal delay. Alternatively, the ventricles may be paced with a constant inter-ventricular delay equal to or substantially equal to the patient's normal inter-ventricular delay. The pacing may be maintained for a fixed number of cycles or period of time. Once the pacing is completed, the process returns.

If in decision block 144 it is determined that there is not a sudden change in the inter-ventricular delay, the process advances to decision block 148 to determine if there has been a gradual increase in inter-ventricular delay to a threshold. By gradual, the increase may be required to have occurred over a greater number of cardiac cycles, such as ten cycles or more or over a period of time, such as one minute or greater. The threshold may be a finite limit, such as, for example, 150 to 250 milliseconds or an increased percentage of the patient's normal inter-ventricular delay. If it is determined in decision block 148 that there has been a gradual increase in inter-ventricular delay to a threshold, the process proceeds to activity block 146 for pacing the ventricles as previously described to restore inter-ventricular synchrony.

If the outcome of decision block 148 is negative, the process then advances to decision block 150 to determine if there has been a change in ventricular activation sequence from a normal sequence. If there has been a sequence change, the process advances to activity block 152 to restore inter-ventricular synchrony. Here the ventricles are paced to restore synchrony. For example, if the normal sequence is for the right ventricular activation to precede the left ventricular activation, a change in this sequence may be paced with the right ventricle being paced at a time before the left ventricular activation is expected followed by the left ventricle being paced a normal inter-ventricular delay interval thereafter. What is important is that the normally first ventricle to be activated be paced prior to the activation of the other ventricle. Such pacing may be maintained for a fixed number of cycles or a fixed time. Thereafter, the ventricles may be sequentially paced in the normal sequence in a demand mode until it is assured that the normal sequence of activation is restored.

If the outcome of decision block 150 is negative, the process proceeds to decision block 154 to determine if the inter-ventricular delay is unstable. The outcome is positive, for example, if the variability in inter-ventricular delay over a last number of cycles, for example 15–60 cycles, is greater than a certain number, such as 15–25 milliseconds. If it is, the process advances to activity block 156. Here the ventricles are overdrive paced to restore inter-ventricular synchrony. The overdrive pacing may be applied to only the slower chamber to activate, and hence with a shortened inter-ventricular delay. Alternatively, both ventricles may be paced at a rate higher than normal at a shortened inter-ventricular delay with gradual return of both rate and delay to normal for restoring inter-ventricular synchrony.

Figure 5:
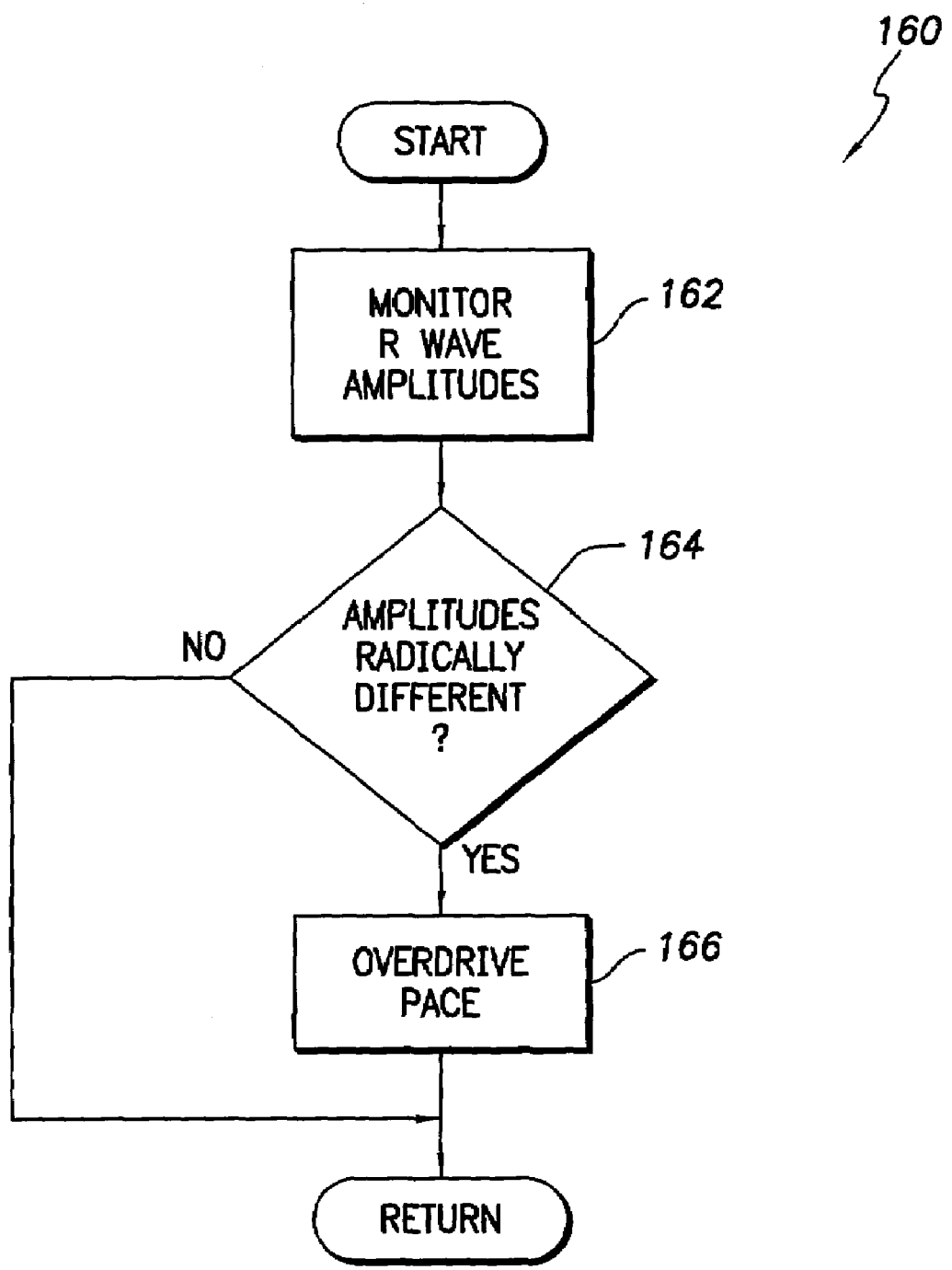
FIG. 5 is a flow chart describing an overview of the operation of a further embodiment of the present invention wherein right ventricular and left ventricular activation amplitudes are monitored and corrective stimulation is applied to the heart.

Referring now to FIG. 5, it shows a flow chart 160 describing a process in accordance with the present invention wherein dissociation of the ventricles is determined by analyzing the amplitudes of the right ventricular and left ventricular activations in the electrogram signals. Hence, in activity block 162 the amplitudes of the right and left ventricular R waves are monitored. Next, in decision block 164 it is determined if the right and left ventricular activation amplitudes, for a same cardiac cycle, are radically different. This may be based upon one amplitude being greater than the other by some factor, such as by a factor of two or more, or by a percentage, for example. If the amplitudes are not radically different, the process returns. If the amplitudes are radically different in one or more cardiac cycles (or X out of Y cardiac cycles), the process then proceeds to activity block 166 wherein the ventricles are overdrive paced. Either ventricle may be paced alone but preferably both ventricles are overdrive paced with a shortened inter-ventricular delay. The rate and delay may then be incrementally returned to normal to return the ventricles to inter-ventricular synchrony.

Figure 6:
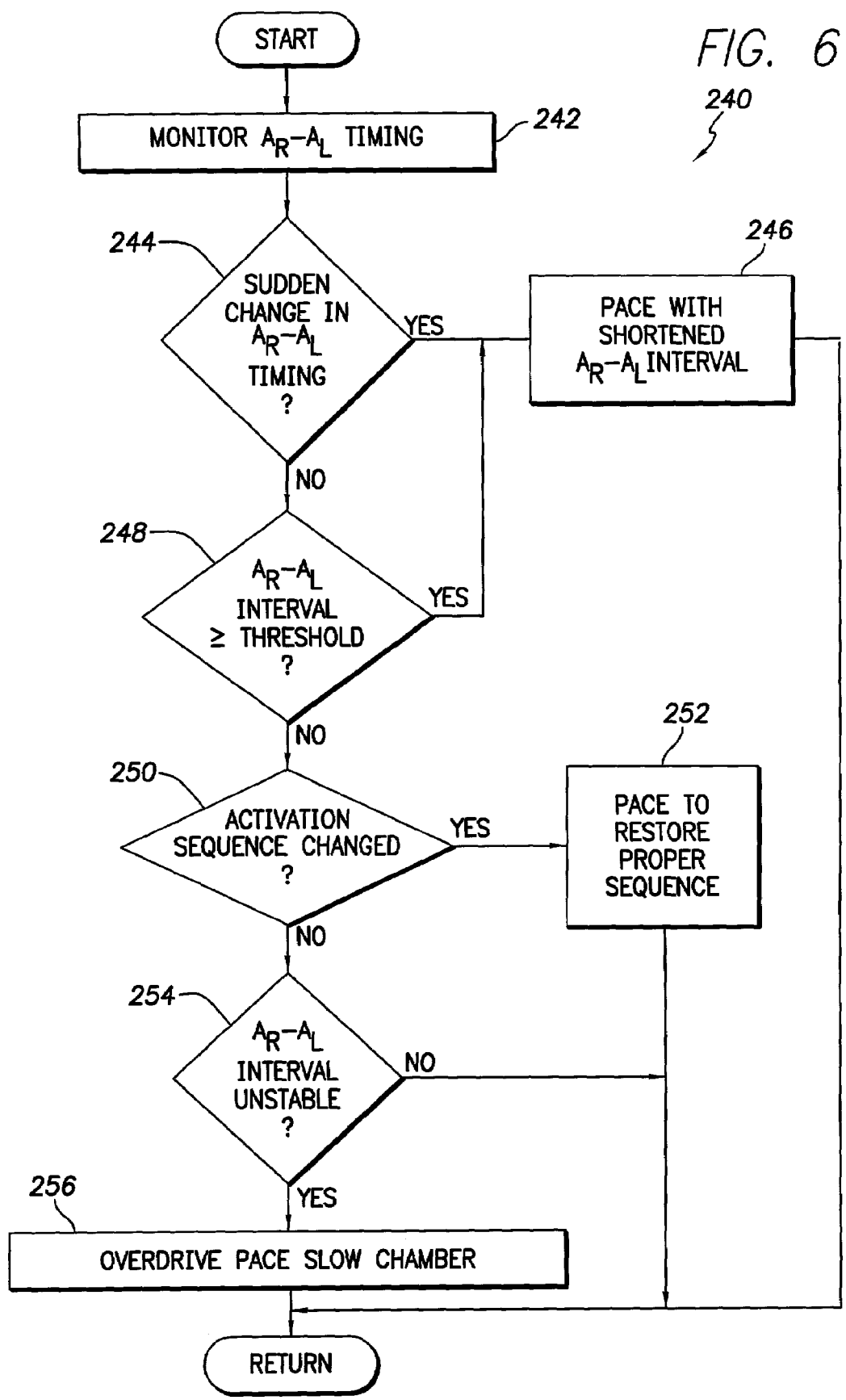
FIG. 6 is a flow chart describing an overview of the operation of another embodiment of the present invention wherein right atrial and left atrial activation timing is monitored and corrective stimulation is applied to the heart.

FIG. 6 shows a flow chart 240 describing an embodiment of the present invention based upon right atrial and left atrial activation timing. Hence the process initiates with the timing of the right atrial and left atrial activations in activity block 242. In decision block 244 it is determined if there has been a sudden change in the inter-atrial delay interval. This determination may be made on a cycle to cycle basis or may be based on a change in the inter-atrial delay over a limited number of cycles, for example, three cycles. The sudden change is preferably an increase of more than, for example 50 to 100 milliseconds. Alternatively the sudden increase may be based upon a percentage of a normal inter-atrial delay of the patient.

If there is a sudden increase in the inter-atrial interval determined in decision block 244, the process advances to activity block 246 for returning the atria to inter-atrial synchrony. Here it is contemplated that the atria be overdriven with a shortened inter-atrial delay. The delay may be less than normal for the patient and may be incrementally increased to a normal delay. Alternatively, the atria may be paced with a constant inter-atrial delay equal to or substantially equal to the patient's normal inter-atrial delay. The pacing may be maintained for a fixed number of cycles or period of time. Once the pacing is completed, the process returns.

If in decision block 244 it is determined that there is not a sudden change in the inter-atrial delay, the process advances to decision block 248 to determine if there has been a gradual increase in inter-atrial delay to a threshold. By gradual, the increase may be required to have occurred over a greater number of cardiac cycles, such as ten cycles or more or over a period of time, such as one minute or greater. The threshold may be a finite limit, such as, for example, 150 to 250 milliseconds or an increased percentage of the patient's normal inter-atrial delay. If it is determined in decision block 248 that there has been a gradual increase in inter-atrial delay to a threshold, the process proceeds to activity block 246 for pacing the atria as previously described to restore inter-atrial synchrony.

If the outcome of decision block 248 is negative, the process then advances to decision block 150 to determine if there has been a change in atrial activation sequence from a normal sequence. If there has been a sequence change, the process advances to activity block 252 to restore inter-atrial synchrony. Here the atria are paced to restore synchrony. For example, if the normal sequence is for the right atrial activation to precede the left atrial activation, a change in this sequence may be paced with the right atrium being paced at a time before the left atrial activation is expected followed by the left atrium being paced a normal inter-atrial delay interval thereafter. What is important is that the normally first atrium to be activated be paced prior to the activation of the other atrium. Such pacing may be maintained for a fixed number of cycles or a fixed time. Thereafter, the atria may be sequentially paced in the normal sequence in a demand mode until it is assured that the normal sequence of activation is restored.

If the outcome of decision block 250 is negative, the process proceeds to decision block 254 to determine if the inter-atrial delay is unstable. The outcome is positive, for example, if the variability in inter-atrial delay over a last number of cycles, for example 15–60 cycles, is greater than a certain number, such as 15–25 milliseconds. If it is, the process advances to activity block 256. Here the atria are overdrive paced to restore inter-atrial synchrony. The overdrive pacing may be applied to only the slower chamber to activate, and hence with a shortened inter-atrial delay. Alternatively, both atria may be paced at a rate higher than normal at a shortened inter-atrial delay with gradual return of both rate and delay to normal for restoring inter-atrial synchrony.

Figure 7:
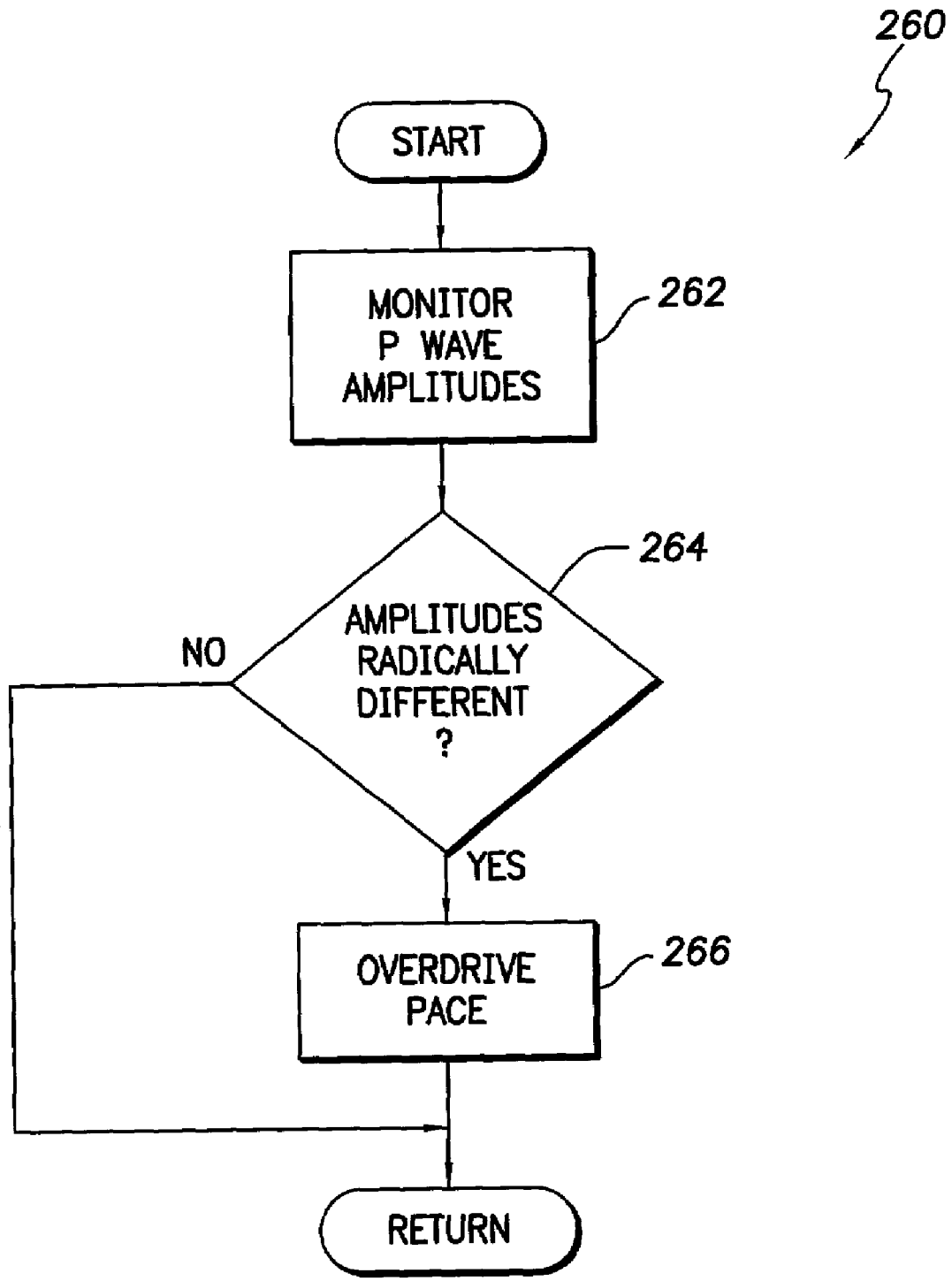
FIG. 7 is a flow chart describing an overview of the operation of a further embodiment of the present invention wherein right atrial and left atrial activation amplitudes are monitored and corrective stimulation is applied to the heart.

Referring now to FIG. 7, it shows a flow chart 260 describing a process in accordance with the present invention wherein dissociation of the atria is determined by analyzing the amplitudes of the right atrial and left atrial activations in the electrogram signals. Hence, in activity block 262 the amplitudes of the right and left atrial P waves are monitored. Next, in decision block 264 it is determined if the right and left atrial activation amplitudes, for a same cardiac cycle, are radically different. This may be based upon one amplitude being greater than the other by some factor, such as by a factor of two or more, or by a percentage, for example. If the amplitudes are not radically different, the process returns. If the amplitudes are radically different for at least one cardiac cycle (or X out of last Y cardiac cycles), the process then proceeds to activity block 266 wherein the atria are overdrive paced. Either atrium may be paced alone but preferably both atria are overdrive paced with a shortened inter-atria delay. The rate and delay may then be incrementally returned to normal to return the atria to inter-atrial synchrony.

While the invention has been described by means of specific embodiments and applications thereof, it is understood that numerous modifications and variations could be made thereto by those skilled in the art without departing from the spirit and scope of the invention. For instance, the disclosed features, either singularly or in groups, could be used with other leads to advantageous results. It is therefore to be understood that within the scope of the claims, the invention may be practiced otherwise than as specifically described herein.

What is claimed is:

1. An implantable cardiac device that returns activations of corresponding right and left chambers of a heart to inter-chamber synchrony comprising:
    a sensing circuit that senses intracardiac signals representing activations of the corresponding right and left chambers;
    a timer that measures a right chamber activation to left chamber activation time during successive cardiac cycles; and
    a pulse generator that stimulates at least one of the right and left chambers to restore inter-chamber synchrony of the right and left chambers responsive to a change in the right chamber to left chamber activation time.

2. The device of claim 1 wherein the corresponding right and left chambers are the right and left ventricles of the heart.

3. The device of claim 2 wherein the predetermined characteristic is a premature ventricular contraction and wherein the detector comprises a premature ventricular contraction detector.

4. The device of claim 3 wherein the pulse generator is configured to apply a stimulation pulse to one of the right ventricle and left ventricle responsive to the detector detecting a premature ventricular contraction in the other one of the right ventricle and left ventricle.

5. The device of claim 4 wherein the pulse generator is a pacing pulse generator.

6. The device of claim 5 wherein the pacing pulse generator delivers a pacing pulse to the one of the right ventricle and left ventricle an inter-ventricular delay time after the detector detects a premature ventricular contraction in the other one of the right ventricle and left ventricle.

7. The device of claim 2 wherein the pulse generator overdrive paces one of the right and left chambers with a shortened inter-ventricular delay to restore inter-chamber synchrony of the right and left chambers responsive to a change in the right chamber to left chamber activation time.

8. The device of claim 7 wherein the change in right ventricular activation to left ventricular activation time is an increase in right ventricular activation to left ventricular activation time.

9. The device of claim 8 wherein the increase is a sudden increase.

10. The device of claim 8 wherein the increase is a gradual increase to a threshold value.

11. The device of claim 7 wherein the change is instability in the right ventricular activation to left ventricular activation time over successive cardiac cycles.

12. The device of claim 2 wherein the predetermined characteristic is a change in order of right ventricular and left ventricular activation from a normal order of right ventricular and left ventricular activation.

13. The device of claim 12 wherein the pulse generator applies pacing pulses to at least one of the right ventricle and left ventricle to restore the order of ventricular activation to the normal order.

14. The device of claim 2 wherein the predetermined characteristic is a relative amplitude difference between a right ventricular activation and a left ventricular activation within at least one common cardiac cycle.

15. The device of claim 14 wherein the pulse generator is a pacing pulse generator that paces at least one of the right ventricle and left ventricle in response to the detector detecting a relative amplitude difference greater than a predetermined factor.

16. The device of claim 15 wherein the pacing pulse generator is an overdrive pacer.

17. The device of claim 15 wherein the pacing pulse generator paces both the right and left ventricle.

18. The device of claim 17 wherein the pacing pulse generator is an overdrive pacer.

19. The device of claim 1 wherein the pulse generator is configured to stimulate the left ventricle a predetermined delay time after a right ventricular activation in response to a change in the right ventricular activation to left ventricular activation time greater than a threshold to restore inter-ventricular synchrony.

20. The device of claim 19 wherein the predetermined delay time is less than a normal right ventricular activation to left ventricular activation time.

21. The device of claim 1 wherein the corresponding right and left chambers are the right and left atria of the heart.

22. The device of claim 21 wherein the predetermined characteristic is a change in right atrial activation to left atrial activation time and wherein the detector comprises a timer that times the right atrial activation to left atrial activation time during successive cardiac cycles.

23. The device of claim 22 wherein the change in right atrial activation to left atrial activation time is an increase in right atrial activation to left atrial activation time.

24. The device of claim 23 wherein the increase is a sudden increase.

25. The device of claim 23 wherein the increase is a gradual increase to a threshold value.

26. The device of claim 22 wherein the change is instability in the right atrial activation to left atrial activation time over successive cardiac cycles.

27. The device of claim 22 wherein the pulse generator is configured to stimulate the left atrium a predetermined delay time after a right atrial activation when the detector detects the change in the right atrial activation to left atrial activation time to restore inter-atrial synchrony.

28. The device of claim 27 wherein the predetermined delay time is less than a normal right atrial activation to left atrial activation time.

29. The device of claim 21 wherein the predetermined characteristic is a change in order of right atrial and left atrial activation from a normal order of right atrial and left atrial activation.

30. The device of claim 29 wherein the pulse generator applies pacing pulses to at least one of the right atrium and left atrium to restore the order of atrial activation to the normal order.

31. The device of claim 21 wherein the predetermined characteristic is a relative amplitude difference between a right atrial activation and a left atrial activation within at least one common cardiac cycle.

32. The device of claim 31 wherein the pulse generator is a pacing pulse generator that paces at least one of the right atrium and left atrium in response to the detector detecting a relative amplitude difference greater than a predetermined factor.

33. The device of claim 32 wherein the pacing pulse generator is an overdrive pacer.

34. The device of claim 32 wherein the pacing pulse generator paces both the right and left atrium.

35. The device of claim 34 wherein the pacing pulse generator is an overdrive pacer.

36. An implantable cardiac device that detects inter-chamber dissociation of a heart and restores inter-chamber synchrony comprising:
sensing means for sensing electrical activity of corresponding right and left chambers of the heart and generating electrical signals representing activations of the corresponding right and left chambers;
timing means for measuring a right chamber to left chamber activation time during successive cardiac cycles; and
stimulating means for applying stimulating pulses to at least one of the corresponding right and left chambers to restore inter-chamber synchrony responsive to a change in the right chamber to left chamber activation time.

37. The device of claim 36 wherein the corresponding right and left chambers are the right and left ventricles.

38. The device of claim 37 wherein the predetermined characteristic is a premature ventricular contraction and wherein the detector means comprises means for detecting premature ventricular contractions responsive to the electrical signals.

39. The device of claim 38 wherein the stimulating means comprises means for applying a stimulation pulse to one of the right ventricle and left ventricle responsive to the detecting means detecting a premature ventricular contraction in the other one of the right ventricle and left ventricle.

40. The device of claim 39 wherein the stimulating means comprises means for providing pacing pulses.

41. The device of claim 40 wherein the stimulating means delivers a pacing pulse to the one of the right ventricle and left ventricle an inter-ventricular delay time after the detecting means detects a premature ventricular contraction in the other one of the right ventricle and left ventricle.

42. The device of claim 37 wherein the stimulating means overdrive paces one of the right and left chambers with a shortened inter-ventricular delay to restore inter-chamber synchrony of the right and left chambers responsive to a change in the right chamber to left chamber activation time.

43. The device of claim 42 wherein the change in the right chamber to left chamber activation time is an increase in the inter-ventricular activation time.

44. The device of claim 43 wherein the increase is a sudden increase.

45. The device of claim 43 wherein the increase is a gradual increase to a threshold value.

46. The device of claim 42 wherein the change in the right chamber to left chamber activation time is instability in the the right chamber to left chamber activation time.

47. The device of claim 37 wherein the predetermined characteristic is a change in ventricular activation order from a normal ventricular activation order.

48. The device of claim 47 wherein the stimulating means comprises means for applying pacing pulses to at least one of the right ventricle and left ventricle to restore the ventricular activation order to the normal order.

49. The device of claim 37 wherein the predetermined characteristic is a relative amplitude difference between a right ventricular activation and a left ventricular activation within at least one common cardiac cycle.

50. The device of claim 49 wherein the stimulating means comprises pacing means for applying pacing pulses to at least one of the right ventricle and left ventricle in response to the detecting means detecting a relative amplitude difference greater than a predetermined factor.

51. The device of claim 50 wherein the pacing means comprises an overdrive pacer.

52. The device of claim 50 wherein the pacing means paces both the right and left ventricle.

53. The device of claim 52 wherein the pacing means is an overdrive pacer.

54. The device of claim 36 wherein the stimulating means comprises means for stimulating the left ventricle a predetermined delay time after a right ventricular activation responsive to the change in the right chamber to left chamber activation time greater than a threshold to restore inter-ventricular synchrony.

55. The device of claim 54 wherein the predetermined delay time is less than a normal right ventricular activation to left ventricular activation time.

56. The device of claim 36 wherein the corresponding right and left chambers are the right and left atria.

57. The device of claim 56 wherein the predetermined characteristic is a change in inter-atrial activation time and wherein the detecting means comprises timing means for timing the time between right atrial activation and left atrial activation during successive cardiac cycles.

58. The device of claim 57 wherein the change in inter-atrial activation time is an increase in the inter-atrial activation time.

59. The device of claim 58 wherein the increase is a sudden increase.

60. The device of claim 58 wherein the increase is a gradual increase to a threshold value.

61. The device of claim 57 wherein the change in inter-atrial activation time is instability in the inter-atrial activation time.

62. The device of claim 57 wherein the stimulating means comprises means for stimulating the left atrium a predetermined delay time after a right atrial activation responsive to the detecting means detecting the change in the inter-atrial activation time to restore inter-atrial synchrony.

63. The device of claim 62 wherein the predetermined delay time is less than a normal right atrial activation to left atrial activation time.

64. The device of claim 56 wherein the predetermined characteristic is a change in atrial activation order from a normal atrial activation order.

65. The device of claim 64 wherein the stimulating means comprises means for applying pacing pulses to at least one of the right atrium and left atrium to restore the atrial activation order to the normal order.

66. The device of claim 56 wherein the predetermined characteristic is a relative amplitude difference between a right atrial activation and a left atrial activation within at least one common cardiac cycle.

67. The device of claim 66 wherein the stimulating means comprises pacing means for applying pacing pulses to at least one of the right atrium and left atrium in response to the detecting means detecting a relative amplitude difference greater than a predetermined factor.

68. The device of claim 67 wherein the pacing means comprises an overdrive pacer.

69. The device of claim 67 wherein the pacing means paces both the right and left atria.

70. The device of claim 69 wherein the pacing means is an overdrive pacer.

71. A method of detecting inter-chamber dissociation of a heart and restoring inter-chamber synchrony to the heart, the method comprising:
    sensing electrical activity of corresponding right and left chambers of the heart and generating electrical signals representing activations of the corresponding right and left chambers;
    measuring a right chamber to left chamber activation time during successive cardiac cycles; and
    applying one or more stimulating pulses to at least one of the corresponding right and left chambers of the heart to restore inter-chamber synchrony responsive to detecting a change in the right chamber to left chamber activation time.

72. The method of claim 71 wherein the corresponding right and left chambers are the right and left ventricles.

73. The method of claim 72 wherein the predetermined characteristic is a premature ventricular contraction and wherein detecting comprises detecting premature ventricular contractions responsive to the electrical signals.

74. The method of claim 73 wherein applying comprises applying a stimulation pulse to one of the right ventricle and left ventricle responsive to detecting a premature ventricular contraction in the other one of the right ventricle and left ventricle.

75. The method of claim 74 wherein applying comprises providing at least one pacing pulse.

76. The method of claim 75 wherein applying comprises delivering a pacing pulse to the one of the right ventricle and left ventricle an inter-ventricular delay time after detecting a premature ventricular contraction in the other one of the right ventricle and left ventricle.

77. The method of claim 72 wherein applying one or more stimulating pulses to at least one of the corresponding right and left chambers of the heart to restore inter-chamber synchrony comprises overdrive pacing one of the right and left chambers with a shortened inter-ventricular delay to restore inter-chamber synchrony of the right and left chambers responsive to a change in the right chamber to left chamber activation time.

78. The method of claim 77 wherein the change in the right chamber to left chamber activation time is an increase in the the right chamber to left chamber activation time.

79. The method of claim 78 wherein the increase is a sudden increase.

80. The method of claim 78 wherein the increase is a gradual increase to a threshold value.

81. The method of claim 77 wherein the change in the right chamber to left chamber activation time is instability in the the right chamber to left chamber activation time.

82. The method of claim 72 wherein the predetermined characteristic is a change in ventricular activation order from a normal ventricular activation order.

83. The method of claim 82 wherein applying comprises applying pacing pulses to at least one of the right ventricle and left ventricle to restore the ventricular activation order to the normal order.

84. The method of claim 72 wherein the predetermined characteristic is a relative amplitude difference between a right ventricular activation and a left ventricular activation within at least one common cardiac cycle.

85. The method of claim 84 wherein applying comprises applying pacing pulses to at least one of the right ventricle and left ventricle in response to detecting a relative amplitude difference greater than a predetermined factor.

86. The method of claim 85 wherein applying comprises overdrive pacing.

87. The method of claim 85 wherein applying comprises applying pacing pulses to both the right and left ventricle.

88. The method of claim 87 wherein applying further comprises overdrive pacing.

89. The method of claim 71 wherein applying comprises stimulating the left ventricle a predetermined delay time after a right ventricular activation responsive to detecting the change in the inter-ventricular activation time to restore inter-ventricular synchrony.

90. The method of claim 89 wherein the predetermined delay time is less than a normal right ventricular activation to left ventricular activation time.

91. The method of claim 71 wherein the corresponding right and left chambers are the right and left atria.

92. The method of claim 91 wherein the predetermined characteristic is a change in inter-atrial activation time and wherein detecting comprises timing the time between right atrial activation and left atrial activation during successive cardiac cycles.

93. The method of claim 92 wherein the change in inter-atrial activation time is an increase in the inter-atrial activation time.

94. The method of claim 93 wherein the increase is a sudden increase.

95. The method of claim 93 wherein the increase is a gradual increase to a threshold value.

96. The method of claim 92 wherein the change in inter-atrial activation time is instability in the inter-atrial activation time.

97. The method of claim 92 wherein applying comprises stimulating the left atrium a predetermined delay time after a right atrial activation responsive to detecting the change in the inter-atrial activation time to restore inter-atrial synchrony.

98. The method of claim 97 wherein the predetermined delay time is less than a normal right atrial activation to left atrial activation time.

99. The method of claim 91 wherein the predetermined characteristic is a change in atrial activation order from a normal atrial activation order.

100. The method of claim 99 wherein applying comprises applying pacing pulses to at least one of the right atrium and left atrium to restore the atrial activation order to the normal order.

101. The method of claim 91 wherein the predetermined characteristic is a relative amplitude difference between a right atrial activation and a left atrial activation within at least one common cardiac cycle.

102. The method of claim 101 wherein applying comprises applying pacing pulses to at least one of the right atrium and left atrium in response to detecting a relative amplitude difference greater than a predetermined factor.

103. The method of claim 102 wherein applying comprises overdrive pacing.

104. The method of claim 102 wherein applying comprises applying pacing pulses to both the right and left atrium.

105. The method of claim 104 wherein applying further comprises overdrive pacing.

* * * * *